United States Patent [19]

Carpenter et al.

[11] 4,416,280
[45] Nov. 22, 1983

[54] CARDIOPLEGIA DELIVERY SYSTEM

[75] Inventors: Walter L. Carpenter, Grass Lake; Bruce A. Amrine, Ann Arbor, both of Mich.

[73] Assignee: Minnesota Mining and Manufacturing Company, St. Paul, Minn.

[21] Appl. No.: 329,604

[22] Filed: Dec. 10, 1981

Related U.S. Application Data

[63] Continuation of Ser. No. 137,716, Apr. 7, 1980, abandoned.

[51] Int. Cl.³ .............................................. A61M 1/03
[52] U.S. Cl. .............................. 128/399; 128/DIG. 3; 604/4; 604/56; 604/113; 604/83
[58] Field of Search .................. 604/4, 6, 93, 250, 113, 604/248, 53, 56, 83; 128/DIG. 3, 399, 400, 401; 417/475; 422/44-48

[56] References Cited

U.S. PATENT DOCUMENTS

| 2,254,994 | 9/1941 | Butland | 128/214 A |
|---|---|---|---|
| 3,064,649 | 11/1962 | Fuson | 128/400 X |
| 3,482,575 | 12/1969 | Claff et al. | 422/45 X |
| 3,533,408 | 10/1970 | Paoli | 128/214 R |
| 3,700,361 | 10/1972 | De Vries | 417/477 |
| 3,737,251 | 6/1973 | Berman et al. | 417/475 X |
| 3,907,504 | 9/1975 | Hammond et al. | 128/DIG. 3 X |
| 3,927,980 | 12/1975 | Leonard | 422/48 |
| 3,941,356 | 3/1976 | Mason | 422/44 X |
| 4,086,924 | 5/1978 | Latham, Jr. | 128/214 R |
| 4,111,209 | 9/1978 | Wolvek et al. | 128/400 |
| 4,249,923 | 2/1981 | Walda | 128/214 A |

FOREIGN PATENT DOCUMENTS

| 2757753 | 6/1979 | Fed. Rep. of Germany | 128/214 A |
|---|---|---|---|
| 852671 | 2/1940 | France | 128/214 A |
| 1546072 | 11/1968 | France | 128/214 |

*Primary Examiner*—C. Fred Rosenbaum
*Assistant Examiner*—Michelle N. Lester
*Attorney, Agent, or Firm*—Cruzan Alexander; Donald M. Sell; Jennie G. Boeder

[57] ABSTRACT

A system for achieving cardioplegia, a protective cessation of the heart muscle activity during open heart surgery which includes providing a circulation system in parallel with the main life support system and deriving a blood source from the arterial reservoir of the main life support system, moving blood from said source through a cooling heat exchanger for selective discharge to the aorta of the heart patient or to a cardiotomy reservoir in the main life support system. The system includes a means for titration of medication to the blood and temperature control and monitoring equipment.

3 Claims, 2 Drawing Figures

CARDIOPLEGIA DELIVERY SYSTEM

This is a continuation, of application Ser. No. 137,716 filed Apr. 7, 1980 now abandoned.

FIELD OF INVENTION

Extracorporeal support systems for cardiovascular surgery and particularly methods and apparatus for cooling the heart during open heart surgery to provide myocardial protection.

BACKGROUND OF THE INVENTION

Open heart surgery has been practiced for a number of years and the techniques for protection of the patient have been under study for all of this period. When the blood of the patient is by-passed to an extracorporeal support system which maintains the pumping function of the heart and the oxygenation function of the lungs, it is important that the heart itself be protected from ischemia, that is, deficiency of blood in the heart muscles, or, in other words, local anemia. In the circumstances of heart surgery, the possibility of damage to the heart is greatly reduced by cooling and administering drugs to the heart in a technique called "cardioplegia". A system for cooling the heart using the actual blood of the patient has also been developed and the use of blood as the vehicle for delivery of the cardioplegia has the advantage of keeping the heart oxygenated while it is arrested for the surgery.

Various methods for achieving cardioplegia have been used such as ice or slush baths with cooling coils submerged therein. Literature on the subject includes:

A Simple Method of Cold Coronary Perfusion Hillel Laks, M.D. et al—The Annals of Thoracic Surgery, Vol. 25, No. 4, Apr. 1978

Cold Cardioplegia Versus Hypothermia for Myocardial Protection. V. R. Conti, M. D. et al, The Journal of Thoracic and Cardiovascular Surgery, Vol. 76, No. 5, Nov. 1978

The present invention relates to an improved system for achieving cardioplegia which utilizes the life support equipment in a combined plan making it easier to control and administer the cold solutions and the drugs which are used in conjunction with the solutions. In previous techniques, the batch system has been used in which a quantity of the patient's blood is mixed with a quantity of medication in a single batch and then introduced into the patient's heart. From time to time, new batches might be requested by the attending surgeon and prepared and administered.

It is an object to provide a cardioplegic system which is more readily controlled and monitored along with the life support system itself and which enables the administration of the solution in a continuous fashion if desired as distinguished from the batch system. The blood pump itself can be used to monitor the cardioplegia flow rate and temperature monitoring is available immediately to an operator. In addition, the administration of drugs along with the cold solution has more reliability and reproducability in this system and apparatus to be disclosed and the mixing of the medication and blood can be achieved in a much more thorough manner than can be done in the batch system.

Thus, an overall consistency in administration can be achieved throughout an entire operation, which sometimes can extend for two or three hours, and also from one patient to another to obtain optimum results at all times.

Other objects and features of the invention will be apparent in the following description and claims in which the principles of the invention are set forth together with a detailed disclosure of the manner and process of using the invention directed to persons skilled in this art to enable the practice of the invention, all in connection with the best mode presently contemplated for the invention.

BRIEF DESCRIPTION OF THE DRAWINGS

Drawings accompany the disclosure and the various views thereof may be briefly described as.

DETAILED SPECIFICATION

Figure 1:
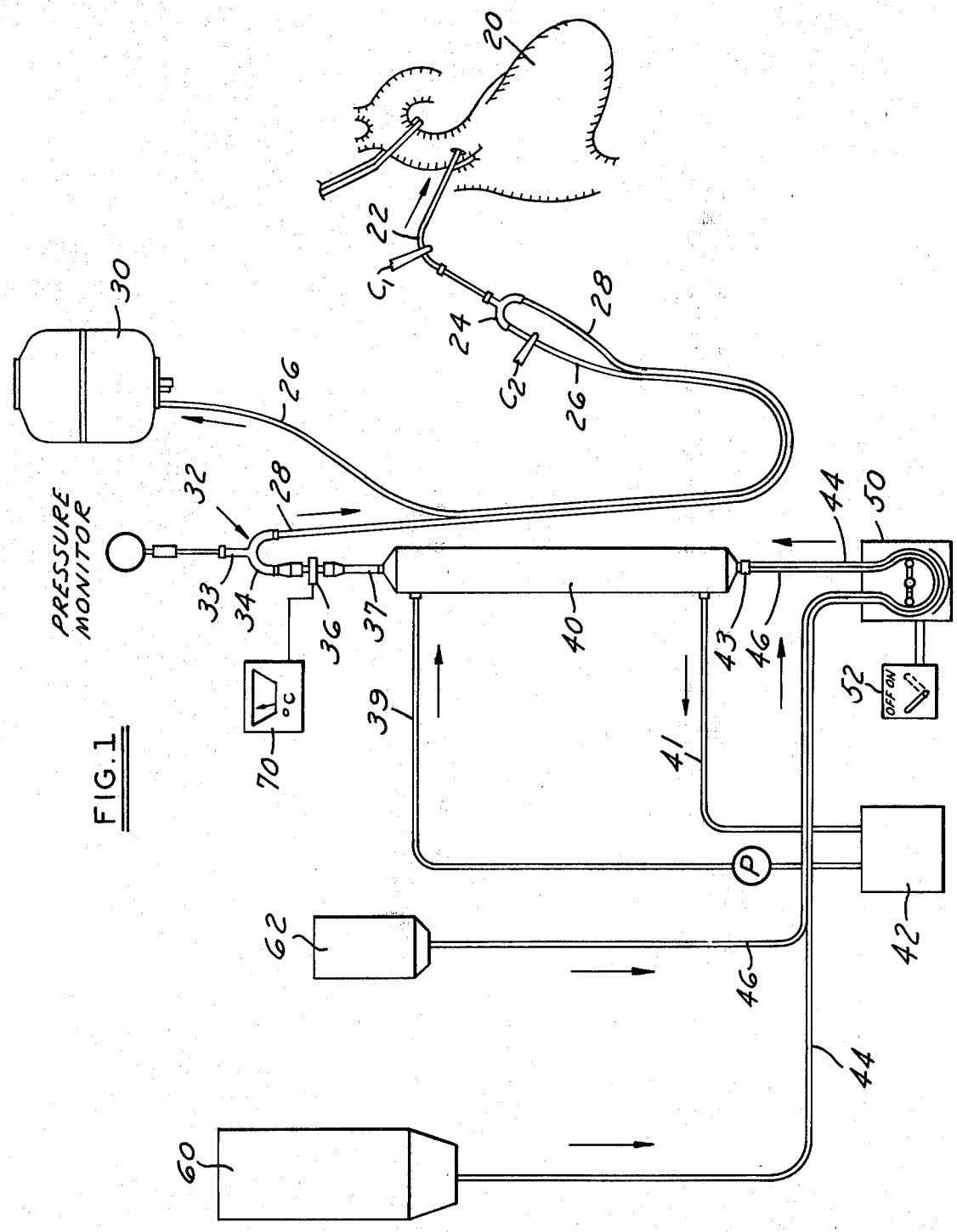
FIG. 1, a generalized view of the system and the various elements of the system.

With reference to FIG. 1, a heart organ is illustrated at 20 with a cannula 22 inserted into the aorta. A "Y" connector 24 connects to two flow tubes 26 and 28. Tube 26 leads to a cardiotomy reservoir 30. Tube 28 leads to a second "Y" connector 32 having a center stem 33 which at its distal end can mount a pressure monitor 33A and can function as a sample port. The inlet branch arm 34 of this connector is connected to a temperature probe 36 at the outlet 37 of a heat exchanger chamber 40 having inlet and outlet conduits 39 and 41, respectively, each leading to a water supply tank 42 which can be refrigerated in any desired way by an ice water bath or mechanical refrigeration to a predetermined temperature. The tank 42 can consist of a coil of tubing in a bath of ice water or can be refrigerated with a thermostatic control. This temperature may range from 5° to 20° Celsius, but the ideal range is believed to be 10° to 15° C. Accurate temperature control is needed for optimum results, but the actual range may differ with the choice of the particular surgical team performing the operation.

The inlet end 43 of the heat exchanger 40 is connected to a double lumen tube 44–46 which passes through a peristaltic pump 50 suitably furnished with guide adaptors and a pump race to accommodate the multiple lumens. The tubes are shown with different diameters and in the illustrated embodiment a ratio of 9 to 1 in tube areas has proved effective, the smaller tube 46 leading from the medication supply. The larger tube may have an effective diameter of 3/16 to ¼" and the diameter of the smaller tube would be about ⅓ of the larger tube. An On-Off switch 52 is provided for the pump. Tube 44 connects to an arterial reservoir 60 containing blood from the patient which, in the main blood circulation system, has been passed through an oxygenator and is ready to be returned to the patient. Tube 46 connects to a chamber 62 containing a cardioplegia agent which is to be added to the fluid flowing to the heart. This material can be potassium or other agents as determined by the practice of the particular doctors and procedures involved in the operation. A controlled release can be provided for the medication in the form of a drop release or other common methods of titration.

The temperature probe 36 is an in-line heat conductive tube to accommodate a temperature recorder constructed in accordance with the disclosure in U.S. Pat. No. 4,091,672 to Amrine and Teders, dated May 30, 1978. A visual reading meter 70 is provided for a rapid check of temperature. The peristaltic pump 50 can be constructed generally in accordance with the pump shown in U.S. Pat. No. 3,700,361 to DeVries, dated Oct. 24, 1972, with a suitable race and guides for the double tube.

The cardiotomy reservoir 30 is used for the collection of blood from the chest cavity by suction. This fluid is filtered and defoamed and returned to the main circuit of the extracorporeal support system. It is also necessary to prime the blood system and the blood used in doing this is also returned to chamber 30 and recirculated through the oxygenator of the main support system.

Figure 2:
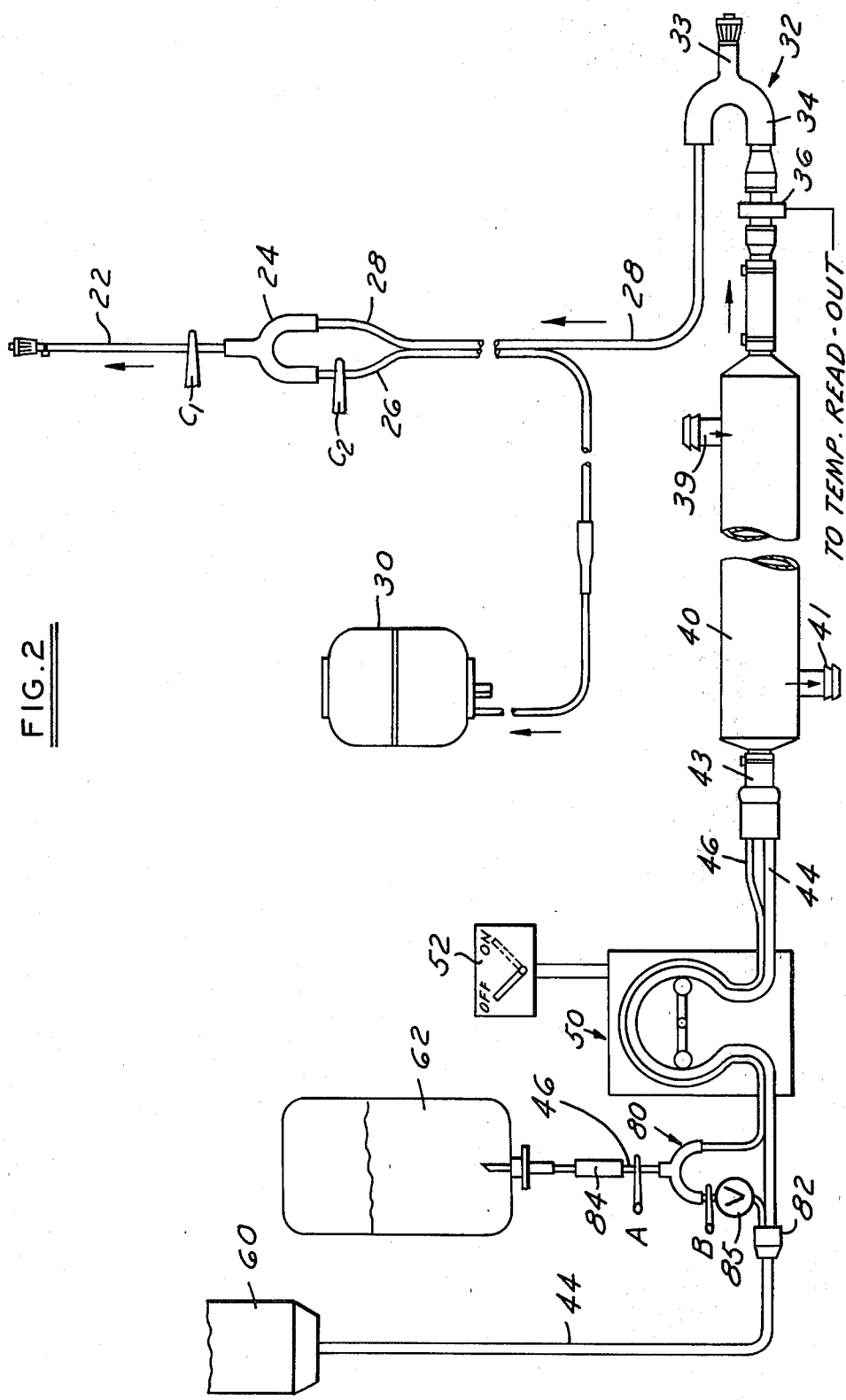
FIG. 2, a more detailed presentation of certain elements of the system.

FIG. 2 illustrates some of the elements of the circuit of FIG. 1 in greater detail. A by-pass circuit is illustrated with a "Y" or wishbone connector 80 having the central stem connected to tube 46 leading from the drug solution tank 62. The tube 44 leading from the arterial reservoir 60 connects to one branch from a split connector 82 and can be closed at B by a surgical clamp. The other branch of the connector 80 connects tube 46 to the pump inlet. A clamp at A will close off the medication supply. A drip chamber 84 is provided below the medication supply 62 to permit observation of the drug flow. Thus, with the clamp A closed and clamp B open, the medication chamber is closed from the circuit. With clamp A open and clamp B closed, the drug supply is open to the pump tube 46. It is also desirable that a unidirectional flow valve be installed in line 85 leading to connector 80 allowing no flow back to the arterial reservoir 60.

OPERATION

The main life support system takes blood from the patient, maintains the temperature, supplies oxygen (oxygenation), and returns the blood to the patient, thus performing the function of the heart and lungs during the operation. The cardioplegia system of the present invention operates in parallel to the main life support system and can be operated continuously or intermittently.

With the switch 52 on and the pump 50 operating, the system may be primed by closing clamp $C_1$ in FIG. 1 and opening clamp $C_2$ to establish full circulation in the various conduits of the cardioplegic system. During this priming stage, it is also desirable to close clamp A at line 46 and open clamp B to allow the by-pass connection 80 to by-pass the medication supply tube 46. Thus, the system may be fully primed without introducing medication into the blood supply. Once this priming is accomplished, the clamps may be changed to open the line to cannala 22 and close by-pass conduit 26 and to open line 46 while closing the by-pass clamp B. Blood is then taken from the arterial reservoir 60 of the main system into tube 44 and passed by the pump to the heat exchanger 40 which reduces the blood temperature to a range between 5° C. and 20° C. In some instances, an initial rapid cooling period is desirable, but the normal operating temperatures for the system is usually in the range of 10° to 15° C. At the same time, a suitable medication, such as potassium, in a titrated quantity, is drawn from the chamber 62 into drip chamber 84 and line 46 and passed through the pump 50 where it mixes in the heat exchanger with the blood from line 46. The cooled mixture passes through the temperature monitor to line 28 and to the cannala 22 into the heart where the cardioplegic function is performed by the mixture of the patient's cooled blood and administered drugs mixed therewith.

The by-pass connection 80 may also be used during periods when it is desirable to interrupt the cardioplegia or the medication flow. Thus, the by-pass systems may be put into operation in the same manner as during the priming to continue the flow of blood while closing off the introduction of medication and by-passing flow to the heart. The drip chamber 84 allows visual monitoring of the medication flow.

The amount of cooling and the frequency of the cooling function will depend on the practice of the particular team performing the operation. Once the cardioplegia system is started, it can be kept operating and the cardioplegic effect controlled by clamps $C_1$ and $C_2$ conveniently close to the operating surgeons. The cardioplegic mixture can be by-passed to the cardiotomy reservoir when not being administered and will be returned to the main support system. The system has the advantage that medication can be introduced into the blood independently by directing the mixture to the patient or to the cardiotomy chamber from which it will go into the main blood support stream. Thus, control of medication can be accomplished in this branch of the overall system. Also, as pointed out, the blood flow may be continued in the cardioplegia system while medication is cut off.

What is claimed as new is as follows

1. A method of obtaining cardioplegia, thereby facilitating open heart surgery, wherein the patient's blood is passed by an external pump through an extracorporeal system and then returned to the patient, the extracorporeal system including devices which temporarily perform the function of the heart and lungs, said method comprising the steps of:
    (a) diverting a proportioned, predetermined flow of the patient's blood from the extracorporeal system into an accessible blood path;
    (b) providing a supply of cardioplegia medication and a medication path into the blood path;
    (c) selectively introducing a proportioned predetermined flow of the cardioplegic medication from the supply through the medication path and into the blood path;
    (d) mixing the blood and the cardioplegic medication;
    (e) passing said mixture of blood and medication through a heat exchanger to cool said mixture to a predetermined temperature;
    (f) directing the cooled mixture of blood and medication, selectively, into the heart of the patient to obtain the desired cardioplegic cooling of the patient's heart by the proportioned and diverted flow of the patient's blood with the cardioplegic medication mixed therein;
    (g) selectively stopping said introduction of a predetermined flow of cardioplegic medication from the medication supply and selectively introducing blood from said blood path into said medication path thereby purging the medication from said medication path; and
    (h) selectively stopping the flow of blood and/or medication to the patient's heart and directing the flow of blood and/or medication to a reservoir.

2. An apparatus for achieving cardioplegia, thereby facilitating open heart surgery during which the patient's blood is extracted and passed by an external pump through an extracorporeal system and then returned to the patient, said extracorporeal system including devices which temporarily perform the function of the heart and lungs while the heart is being repaired, said apparatus comprising:

(a) means for diverting a predetermined flow of blood from the extracorporeal system through an accessible blood path;

(b) a supply of cardioplegic medication, and means for defining a medication path from said medication supply to said blood path;

(c) means for selectively introducing a predetermined quantity of medication from said medication supply through said medication path, and into said blood path, and for mixing the medication with the blood;

(d) a pump in said blood path for moving the blood and medication along said paths;

(e) a heat exchanger in said blood path downstream of said pump for cooling the blood and medication mixture;

(f) a temperature probe in said blood path downstream of said heat exchanger for measuring the temperature of the blood and medication mixture flowing within said blood path;

(g) means for selectively directing the blood and medication mixture to the heart of the patient;

(h) control means operable by an attending physician for stopping the introduction of medication into said medication path and and independent control means for selectively introducing blood from said blood path into said medication path thereby purging the medication from said medication path; and (i) control means operable by an attending physician for stopping the introduction of the blood and/or the blood and medication mixture to the patient's heart and directing the flow of said blood and/or blood and medication mixture to a reservoir.

3. An apparatus as defined in claim 2 in which a peristaltic pump is used as the pump for the blood and medication and a double lumen forms at least a part of said blood path, the lumen being proportioned in area to provide a desired flow ratio of the blood in the blood path to the medication in the medication path.

* * * * *